United States Patent [19]

Wheeler et al.

[11] Patent Number: 4,946,956

[45] Date of Patent: Aug. 7, 1990

[54] ARYLENEDIAMINE SUBSTITUTED PYRIMIDINES

[75] Inventors: Edward L. Wheeler, Watertown; Franklin H. Barrows, Waterbury; Robert J. Franko, Beacon Falls, all of Conn.

[73] Assignee: Uniroyal Chemical Company, Inc., Middlebury, Conn.

[21] Appl. No.: 247,143

[22] Filed: Sep. 21, 1988

[51] Int. Cl.$^5$ ............................................ C07D 239/02
[52] U.S. Cl. ...................................... 544/323; 544/296; 544/310; 544/312; 544/317; 544/324; 544/326; 544/327; 544/328; 544/329; 524/100
[58] Field of Search ............... 544/296, 310, 312, 317, 544/323, 324, 326, 327, 328, 329

[56] References Cited

FOREIGN PATENT DOCUMENTS 0233982 9/1988 Japan ..................................... 544/310

Primary Examiner—Mary C. Lee
Assistant Examiner—J. Richter
Attorney, Agent, or Firm—Raymond D. Thompson

[57] ABSTRACT

Disclosed are novel 2,4,6 substituted pyrimidines where the substituents may be the same or different groups. At least one substituent must be N-alkyl par-phenylenediamino, and the other substituents may be various radicals containing sulfur, oxygen or nitrogen or hydrogen or alkyl groups. The compounds are useful as antioxidants and antiozonants for unsaturated compounds and polymers.

2 Claims, No Drawings

ARYLENEDIAMINE SUBSTITUTED PYRIMIDINES

BACKGROUND OF THE INVENTION

This invention relates to new pyrimidine compounds which are useful as antiozonants for rubber, processes for their manufacture, and to their use in inhibiting the deteriorating effect of ozone on unsaturated polymers.

The novel compounds of the invention may also be useful as stabilizers in lubricating oils and greases and natural or synthetic fats and oils. Thermoplastic polymers may also be stabilized against thermal and oxidative degradation and viscosity breakdown during processing.

It is well known that ozone causes surface cracking of conventional highly unsaturated rubber vulcanizates when the rubber is placed under strain in an ozone environment. The most severe deterioration occurs when a small number of cracks are formed which grow rapidly into deep, disruptive fissures. These ozone cracks seriously shorten the serviceable life of the article.

The rubber articles which may achieve lower service lives through the use of the novel compounds of the invention include hoses, belts, airsprings, sheeting, seals, gaskets, mounts, bridge pads and other mechanical goods.

Chemical antiozonants have been developed which retard the formation of the ozone cracks occurring under static and dynamic conditions. Examples of antiozonants in common use include the substituted paraphenylenediamine class of compounds.

The use of the well known paraphenylenediamine materials has improved ozone protection under both static and dynamic conditions, however, even the best of the class just described have a very strong tendency to both stain and discolor. The term "stain" or "staining" is herein used to describe the characteristic of a material to diffuse through a polymeric substrate and discolor the adjacent surface. This diffusion staining is highly objectionable in most light colored rubber articles. In tires, which is the largest application in which the ozone protection is required, the tendency to diffusion staining of the aforementioned paraphenylenediamine materials is objectionable particularly in white sidewall type tires. Even in non-white sidewall type tires, the tendency of the materials to diffuse to the surface of the tire sidewall can be objectionable in that a brown, dull surface is created on the tire sidewall. This is aesthetically objectionable in that it detracts from the general jet black, smooth appearance of a new tire. It is obvious that in a white sidewall tire, the migration of the brown discoloring material to the surface of the white sidewall is highly objectionable and generally difficult to remove during cleaning of the tire surface.

An object of this invention is to provide an antiozonant material which is highly effective in protecting a highly unsaturated polymer substrate from ozone attack. A further object is to provide ozone protection in a static condition at very low levels and to protect the rubber article during extended aging conditions against ozone attack. Yet another object is to produce a compound which does slowly diffuse and does not produce an objectionable brown bloom.

The novel arylenediamine substituted pyrimidine compounds of the invention have provided exceptional long term ozone protection under static conditions. An advantage of the substituted pyrimidine compounds is that it produces a substantially non-staining antiozonant of high molecular weight. A further advantage is that it slowly blooms to the surface of the rubber article. A further advantage is that the pyrimidine compounds of the invention provide outstanding dynamic protection without the use of waxes preferably by blending said pyrimidine compounds with other known antiozonants and antioxidants.

BRIEF DESCRIPTION OF THE INVENTION

The object and advantages of the invention may be obtained using a compound of the general formula:

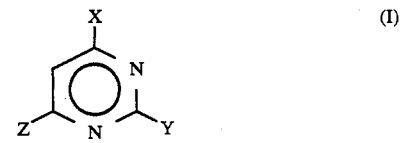

in which

$R^1$ is hydrogen, $C_1$-$C_{11}$ alkyl, $C_3$-$C_6$ cycloalkyl, phenyl or phenyl substituted with $C_1$-$C_4$ alkyl or phenyl;

$R^2$ is $C_1$-$C_{11}$ alkyl, $C_3$-$C_6$ cycloalkyl or

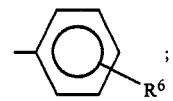

$R^3$ is hydrogen, phenyl or $C_1$-$C_{11}$ alkyl, when $R^1$ is hydrogen;

$R^4$ is hydrogen or $C_1$-$C_8$ alkyl:

$R^5$ is hydrogen or $C_1$-$C_8$ alkyl:

$R^6$ is hydrogen, $C_1$-$C_{11}$ alkyl or $C_1$-$C_4$ alkoxy

Y is X, hydrogen, $C_1$-$C_4$ alkyl, —SH, $SR^7$, —OH, $OR^7$,

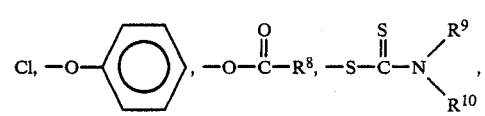

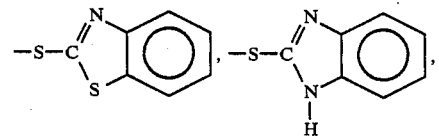

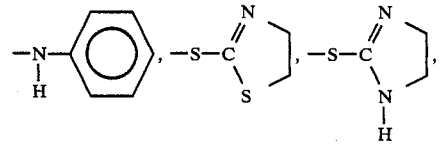

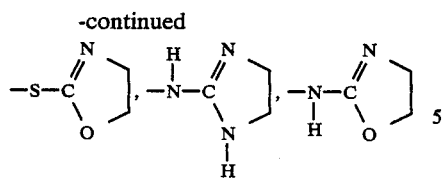

$R^7$ is $C_1-C_{12}$;
$R^8$ is $C_1-C_{11}$;
$R^9$ and $R^{10}$ are $C_1-C_4$ alkyl

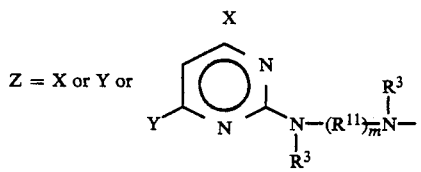

$R^{11}$ is $C_2-C_{10}$ linear alkyl; $C_5-C_{10}$ cycloalkyl or $C_7-C_9$ phenylalkyl;
m is 2-6
If $Y \neq X$ then $R_6$ can be hydrogen.

The novel compounds of the present invention may be prepared by a process comprising:

reacting an N-substituted-p-phenylenediamine with a tri-halopyrimidine in a solvent to form a reaction mixture including a 2,4,6-tris(N-substituted-p-phenylenediamino)-pyrimidine trihydrohalide; and neutralizing said 2,4,6-tris(N-substituted-p-phenylenediamino)-pyrimidine trihydrohalide with a base to form a 2,4,6-tris(N-substituted-p-phenylenediamino) pyrimidine.

Unsaturated polymers may be stabilized against ozone degradation by incorporation therein of an effective amount the novel compounds of structure (I).

DETAILED DESCRIPTION OF THE INVENTION

Referring now to structure (I), the preferred compositions are those in which X, Y and Z are N-substituted linear or branched $C_3-C_{18}$ alkyl-p-phenylenediamine groups. The alkyl groups more preferred are those with a secondary carbon in the alpha position to the nitrogen. In this configuration, the antiozonant activity of the compound is believed to be enhanced. Therefore, the more preferred alkyl groups are branched chains which provide an alkyl substituent which is in accordance with this configuration. The cycloalkyl or $C_1-C_{12}$ alkyl substituted cycloalkyls provide such a alpha carbon configuration as well. The structure of formula I which is most preferred at this time are compounds in which $R^2$ is a $C_6-C_8$ branched chain alkyl group. Examples of some preferred chemicals of the present invention are: 2,4,6-tris(N-1,4-dimethylpentyl-p-phenylenediamino)-pyrimidine; 2,4,6-tris(N-isopropyl-p-phenylenediamino)pyrimidine; 2,4,6-tris(N-cyclohexyl-p-phenylenediamino)pyrimidine; 2,4,6-tris(N-sec-butyl-p-phenylenediamino)pyrimidine; 2,4,6-tris(N-1,3-dimethylbutyl-p-phenylenediamino)pyrimidine; 2,4,6-tris(N-1-methylheptyl-p-phenylenediamino)pyrimidine. The most preferred material 2,4,6-tris(N-1,4-dimethylpentyl-p-phenylenediamino)pyrimidine.

The compounds of the invention can by synthesized advantageously by the following general method. Although the reagents may be added in different order, the preferred method is as follows:

In the case of the 2,4,6-tris(N-substituted-p-phenylenediamino)pyrimidines, three plus moles of the N-substituted-p-phenylenediamine, which is prepared by methods known to those familiar with the art, in a suitable solvent such as isobutanol, are reacted with a molar equivalent of 2,4,6-trihalogenopyrimidine, at 10°–30° C. with appropriate cooling. The reaction mixture is then heated to reflux in order to complete the displacement of the halogen atoms. After 3–40 hours at reflux the formation of the 2,4,6-tris(N-substituted-p-phenylene-diamino)pyrimidine trihydrochloride is complete.

The process is unique in that the basicity of the substituted-p-phenylenediamine allows the displaced halogen atom of the halogenopyrimidine to form the hydrohalide directly thereby enabling isolation of the trihalide and effecting a purification step.

The tris-hydrochloride may be removed by filtration, then reslurried in a suitable water miscible solvent, neutralized with aqueous base such as sodium hydroxide, and crystallized from the aqueous solvent mixture.

If the starting N-substituted-p-phenylenediamine is sufficiently pure, or a less pure product is acceptable, isolation of the tris-hydrochloride is not necessary, and the reaction mixture can be neutralized and the product crystallized and isolated by filtration.

The 2,4-bis(N-substituted-p-phenylenediamino)-6-substituted pyrimidines are synthesized in a like manner, except two plus moles of the N-substituted-p-phenylene-diamine are reacted with a molar equivalent of 2,4-di-halogeno-6-substituted pyrimidine.

Temperature control of the reaction is of some importance. It is preferred that the first stage of the reaction take place at or below 30° C. and that the second stage take place at least 30° C. above the first stage. Selection of the optimal temperatures are, of course, dependent upon the identity of the p-phenylenediamine and solvent which is chosen.

Preferred solvents are alcohols although any suitable solvent may be utilized. The term solvent is meant to include an excess of the N-substituted-p-phenylenediamine which may serve to solvate the reaction product and allow subsequent isolation.

It is noted here that any use of the term "alkyl", in the context of a starting material (i.e., N-alkyl-p-phenylenediamine) or the final substituted pyrimidine compounds of this invention, is deemed to include cycloalkyl and alkyl substituted cycloalkyl structures as well.

The compounds of the invention are most advantageously utilized as antiozonants to protect highly unsaturated polymers such as natural or synthetic elastomers. Representative of the highly unsaturated polymers which may be employed in the practice of this invention are diene elastomers. Such elastomers will typically possess an iodine number of between about 100 and about 250, although highly unsaturated rubbers having a higher or a lower (i.e., of 50–100) iodine number may also be employed. Illustrative of the diene elastomers which may be utilized are polymers based on conjugated dienes such as 1,3-butadiene; 2-methyl-1,3-butadiene; 1,3-pentadiene; 2,3-dimethyl-1,3-butadiene; and the like, as well as copolymers of such conjugated dienes with monomers such as styrene, alpha-methylstyrene, acrylonitrile, methacrylonitrile, methyl acrylate, ethyl acrylate, methyl methacrylate, ethyl methacrylate, vinyl acetate and the like. Preferred highly unsaturated rubbers include natural rubber, cis-polyisoprene, polybutadiene, poly(styrenebutadiene), polychloroprene and poly(acrylonitrilebutadiene). Moreover, mixtures of two or more highly unsaturated rubbers may be employed. Also, mixtures of the highly unsaturated rubbers with elastomers having lesser unsaturation such as EPDM, EPR, butyl or halogenated butyl rubbers are also within the contemplation of the invention.

These lesser unsaturation polymers generally have iodine numbers below 100 and preferably between about 10 and 100. The most preferred range is between 20 and 40. The most preferred lesser unsaturated polymers are the ethylene/propylene/diene terpolymers (EPDM) utilizing non-conjugated dienes such as 1,4-hexadiene; ethylidene norbornene, dicyclopentadiene and others well known in the art. The amount of EPDM in the elastomeric composition is from about 15 to about 50 parts by weight per 100 parts by weight of the total elastomers.

The novel compounds of the invention may be used in combination with other antiozonants and/or with microcrystalline waxes as are commonly used to protect against static ozone attack. The other antiozonants which may be utilized include any of the commonly recognized paraphenylenediamine class of materials: N-phenyl-N'-(1,3-dimethylbutyl)-p-phenylenediamine; N-phenyl-N'-isopropyl-p-phenylenediamine; N-phenyl-N'-(1-methylheptyl)-p-phenylenediamine; N-phenyl-N'-cyclohexyl-p-phenylenediamine; mixed diaryl-p-phenylenediamines; N,N'-diphenyl-p-phenylenediamine; N,N'-di-beta-naphthyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N-phenyl-N'-p-toluenesulfonyl-p-phenylenediamine; N-phenyl-N'-alkyl-p-phenylenediamine; 6-ethoxy-1,2-dihydro-2,2,4-trimethylquinoline; and nickel dibutyl dithiocarbamate.

A more preferred antiozonant to be used in combination with the novel pyrimidine compounds of the invention is N-phenyl-N'-(1,3-dimethylbutyl)-p-phenylenediamine.

The new class of tris(N-alkyl-p-phenylene diamino)-1,3,5 triazine disclosed in copending U.S. application Nos. 9,0298, 163,921, 163,924 are preferred materials for blending with the compounds of this invention, for improving the overall balance of static and dynamic ozone protection.

The highly unsaturated polymers to be protected may be formulated in conventional manner with the many usual compounding ingredients, for example, vulcanizing agents, accelerators, activators, retarders, antiozonants, antioxidants, plasticizing oils and softeners, fillers, reinforcing pigments and carbon blacks.

The novel compounds of the invention may be added to a unsaturated polymer at a level of from 0.1 to about 10 parts by weight per hundred parts by weight of rubber hydrocarbon (hereinafter PHR). For these purposes the polymer is assumed to be a natural or synthetic rubber. A more preferred addition level is about 1 to about 6 PHR. The most preferred level is from about 2 to about 4 PHR. When the pyrimidine compounds of the invention are used in combination with other antiozonants such as the paraphenylenediamine class of materials, they may be added in a blend which totals to the ranges set forth above. The compounds of the invention may be blended with the other antiozonants at ratios ranging from 1:3 to 3:1. More preferred is a ratio range of 2:3 to 3:2. These ratios are meant to indicate the percentages are 40:60 to 60:40 where in all cases the pyrimidine compounds of the invention are the first number of each ratio. It should be noted that in certain applications and with certain other antiozonants, the PHR ranges of antiozonant listed above may be varied in order to obtain the optimal protection. Reasonable experimentation must be undertaken in order to optimize the ratios and overall levels of the blend when the pyrimidine compounds of the invention are blended with other conventional antioxidants and antiozonants.

The novel pyrimidine compounds of the invention may be synthesized by a suitable synthesis route. The following synthesis examples are provided to illustrate a currently preferred method of manufacturing certain of the class of pyrimidine compounds of the invention.

SYNTHESIS EXAMPLES

EXAMPLE 1

Preparation of 2,4,6-tris(N-1,4-dimethylpentyl-p-phenylenediamino)-pyrimidine.

In a one liter, four necked, round-bottomed flask equipped with a thermometer, a mechanical stirrer, and a condenser, was placed a solution of 68 grams (0.33 mole) of 4-amino-N-(1,4-dimethylpentyl)aniline in 200 ml of isobutanol. The temperature of the solution was adjusted to 30° C. and 18.4 grams (0.10 mole) of 2,4,6-tri-chloropyrimidine was added over ¼ hour period as the reaction temperature rose to 45° C. The reaction mixture was refluxed for 40 hours. The reaction was followed by high performance liquid chromatography (HPLC) by observing the disappearance of the starting amine, and the conversion of the intermediate mono- and bis-substituted compounds to the final tris-substituted product. After cooling to 60° C., 120 grams (0.30 mole) of 10 percent sodium hydroxide solution was added dropwise over ½ hour period. The water layer was removed and discarded. The isobutanol layer was extracted with 100 ml. of water. The title compound precipitated upon cooling and was isolated by filtration and washed with isobutanol. The product was taken up in toluene, extracted with water, and reprecipitated by adding an equal volume of hexane. It melted at 138°–141° C. The yield was 69.4 percent. The infrared spectrum was consistent with the structure. Relative area HPLC analysis of the product showed it to be 94.7 percent pure.

EXAMPLE 2

Preparation of 2,4,6-tris(N-1-methylheptyl-p-phenylenediamino)-pyrimidine

The procedure of Example 1 was repeated except on a 0.13 molar scale with 4-amino-N-methylheptyl)aniline used to produce the title compound m.p. 87°–89° C. The yield was 54 percent. The infrared spectrum was consistent with the structure. Relative area HPLC analysis of the product showed it to be 95.9 percent pure.

EXAMPLE 3

Preparation of 2,4,6-tris(N-isopropyl-p-phenylene-diamino)pyrimidine.

In a one liter, four-necked, round-bottomed flask equipped with a thermometer, a mechanical stirrer, a condenser, and a dropping funnel was placed a solution of 75 grams (0.50 mole) of 4-amino-N-(isopropyl)aniline in 300 ml. of isobutanol. The temperature of the solution was adjusted to 10° C. and 23 grams (0.125 moles) of 2,4,6-trichloropyrimidine was added over ½ hour period keeping the temperature at 10° C. The reaction mixture was refluxed for 20 hours. The reaction was followed by HPLC by observing the disappearance of the starting amine, and the conversion of the intermediate mono- and bis-substituted compounds to the final tris-substituted product. The reaction mixture was cooled to 10° C. and poured into 500 ml. of acetonitrile. The trihydrochloride of the title compound precipitated and was removed by filtration. The trihydrochloride was charged back to the reaction flask, and 375 ml. of a 10 percent aqueous isopropanol solution was added. The temperature of the solution adjusted to 60° C. and 60 grams (0.375 mole) of 25 percent sodium hydroxide solution was added. Upon cooling to 10° C., the title compound precipitated and was isolated by filtration. It melted at 210°–212° C. The yield was 64.1 percent. The infrared spectrum was consistent with the structure. Relative area HPLC analysis of the product showed it to be 92.1 percent pure.

EXAMPLE 4

Preparation of 2,4,6-tris(N-phenyl-p-phenylenediamino) pyrimidine

The procedure of Example 3 was repeated except on a 0.15 molar scale with 4-amino-N-(phenyl)aniline used to produce the title compound m.p. 198°–202° C. The yield was 53.2 percent. The infrared spectrum was consistent with the structure. Relative area HPLC analysis of the product showed it to be 90.5 percent pure.

EXAMPLE 5

Preparation of 2,4,6-tris(N-2,6-dimethylheptyl-p-phenylenediamino)-pyrimidine.

In a one liter four-necked, round-bottomed flask equipped with a thermometer, a mechanical stirrer, and a condenser was placed a solution of 84.2 grams (0.36 mole) of 4-amino-N-(2,6-dimethylheptyl)aniline in 200 ml. of isobutanol. The temperature of the solution was adjusted to 20° C. and 18.4 grams (0.10 mole) of 2,4,6-trichloropyrimidine was added over ½ hour period at 20° C. The reaction mixture was refluxed for 18 hours. The reaction was followed by HPLC by observing the disappearance of the starting amine, and the conversion of the intermediate mono- and bis-substituted compounds to the final tris-substituted product. After cooling to 60° C. 120 grams (0.30 mole) of 10 percent sodium hydroxide solution was added The water layer was removed and discarded. The title compound precipitated upon cooling with the addition of water, and was isolated by filtration, m.p. 123°–126° C. The yield was 72.2 percent. The infrared spectrum was consistent with the structure. Relative area HPLC analysis of the product showed it to be 92.1 percent pure.

EXAMPLE 6

Preparation of 2,4 bis(N-isopropyl-p-phenylenediamino)6-methylpyrimidine.

In a one liter, four-necked, round-bottomed flask equipped with a thermometer, a mechanical stirrer, and a condenser was placed a solution of 75 grams (0.50 mole) of 4-amino-N-(isopropyl)aniline in 250 ml. of isopropanol. The temperature of the solution was adjusted to 20° C. and 31.6 grams (0.20 mole) of 2,4-dichloro-6-methylpyrimidine was added over ¼ hour period at 20° C. The reaction mixture was heated to 45° C. for 1 hour, then refluxed for three hours. The reaction was followed by HPLC by observing the disappearance of the starting amine, and the conversion of the intermediate mono-substituted compound to the final bis-substituted product. The reaction mixture was cooled to 20° C., and the dihydrochloride of the title compound was removed by filtration. The dihydrochloride was charged back to the reaction flask, and 400 ml. of 25 percent aqueous isopropanol was added. The temperature of the solution was adjusted to 60° C. and 32 grams (0.40 mole) of 50% sodium hydroxide solution was added After stirring at 60° C. for 1 hour period the water layer was removed. The title compound was precipitated at 50° C. by the drop-wise addition of water, and was removed by filtration. It melted at 168°–170° C. The yield was 79.7 percent. The infrared spectrum was consistent with the structure. Relative area HPLC analysis of the product showed it to be 93.2 percent pure.

EXAMPLE 7

Preparation of 2,4-bis(N-sec-butyl-p-phenylenediamino) 6-methylpyrimidine.

The procedure of Example 6 was repeated except 4-amino-N-(sec-butyl)aniline was used to produce the title compound, m.p. 139°–141° C. The yield was 87.3 percent. The infrared spectrum was consistent with the structure. Relative area HPLC analysis of the product showed it to be 95.2 percent.

EXAMPLE 8

Preparation of 2,4,6-tris(N-1,4-dimethylpentyl-2-methyl-p-phenylenediamino)pyrimidine.

In a one liter, four-necked, round-bottomed flask equipped with a thermometer, a mechanical stirrer, and a condenser was placed a solution of 176 grams (0.80 mole) of 4-amino-N-(1,4-dimethylpentyl)2-methylaniline in 500 ml. of isopropanol. The temperature of the solution was adjusted to 25° C. and 36.6 grams (0.20 mole) of 2,4,6-tri-chloropyrimidine was added over ¼ hour period at 25° C. The reaction mixture was held for one hour at 25° C., then refluxed for 40 hours. The reaction was followed by HPLC by observing the disappearance of the starting amine, and the conversion of the intermediate mono- and bis-substituted compounds to the final tris-substituted product. After cooling to 60° C. 120 grams (0.60 mole) of 20 percent sodium hydroxide solution was added dropwise over ½ hour period. The water layer was removed and discarded. The isopropanol layer was extracted with 100 ml of water. The isopropanol solution was stripped. The residue was crystallized in hexane. The title compound was isolated by filtration, m.p. 83°–85° C. The yield was 70.8 percent. The infrared spectrum was consistent with the structure. Relative area HPLC analysis of the product showed it to be 93.2 percent pure.

EXAMPLE 9

Preparation of 2,4-bis(N-1,4-dimethylpentyl-p-phenylenediamino)6-methylpyrimidine.

In a one liter, three-necked, round-bottom flask equipped with a thermometer, a mechanical stirrer, and a condenser, was placed a solution of 105 grams (0.51 mole) of 4-amino-N-(1,4-dimethylpentyl)aniline in 400 ml. of isopropanol. The temperature of the solution was adjusted to 20° C. and 40.75 grams (0.25 mole) of 2,4-dichloro-6-methylpyrimidine was added over ½ hour period at 20°-25° C. The reaction mixture was refluxed for 6 hours. The reaction was followed by HPLC by observing the disappearance of the starting amine, and the conversion of the intermediate mono-substituted compound to the final bis-substituted product. The dihydrochloride of the title compound precipitated and was removed by filtration. A slurry of 35 grams (0.06 mole) of the dihydrochloride in 200 ml. of toluene was neutralized with a 30 percent sodium hydroxide solution at 55°-60° C. The water layer was removed, and the toluene layer extracted with water. The toluene layer was stripped to dryness and recrystallized from isopropanol to give the title compound m p. 83°-85° C. The yield was 55.8 percent. The infrared spectrum was consistent with the structure. Relative area HPLC analysis of the product showed it to be 94.7 percent pure.

TABLE I

DYNAMIC OZONE TESTING
Continuing Flexing
(Results in Kilocycles)

| EXAMPLE NO. | 10 | 11 | 12 | 13 | 14 |
|---|---|---|---|---|---|
| ANTIOZONANT | blank | Ex. 1 | Ex. 2 | Ex. 3 | Ex. 4 |
| Unaged | | | | | |
| OK | — | — | — | — | — |
| VVS | 529 | 1513 | 1513 | 1513 | 529 |
| VS | — | 4308 | 3041 | 4308 | — |
| S | 3041 | 6324 | 4479 | 4479 | 3041 |
| C | 4308 | * | 5330 | 5330 | 4308 |

OK = no cracks
VVS = very, very slight cracks
VS = very slight cracks
S = slight cracks
C = cracked
*Test ongoing

ANTIOZONANT UTILITY EXAMPLES 10-19

The N-substituted arylenediamino pyrimidine compounds of the invention function as outstanding antiozonants in rubber polymers with no migratory staining tendency evident at this time. The following examples demonstrate their utility in a variety of ozone and color stability test regimes. All tests utilize the pyrimidines in vulcanized rubber compounds as are typical in the industry. The following test formulation is a typical rubber compound.

TEST FORMULATION

| | Parts by Weight |
|---|---|
| Natural Rubber (SMR5CV) | 50.0 |
| Polybutadiene (cis 1,4 BR) | 50.0 |
| Carbon Black (N-326) | 50.0 |
| Zinc Oxide | 3.0 |
| Microcrystalline Wax | 1.5 |
| Stearic Acid | 1.0 |
| Aromatic Oil | 5.0 |
| Benzothiazole Sulfenamide | 1.0 |
| Sulfur | 2.0 |

-continued

TEST FORMULATION

| | Parts by Weight |
|---|---|
| Antiozonant - Variable | Variable |

The foregoing test formulation was used for all test samples unless otherwise noted. The formulation is an approximation of a typical tire sidewall compound. The identity and level of the antiozonant are the variables to be evaluated in the subsequent examples.

The test formulation was utilized to make uncured test sheets by preblending the natural rubber and polybutadiene. Once blending was accomplished, all other ingredients except the sulfur and benzothiazole sulfenamide were added to form a nonproductive compound and in a subsequent mixing step, the foregoing ingredients were added. Tests sheets for the subsequent testing were cured in a platen press between heated plates for a time sufficient to achieve full cure. For the purposes of testing, a fifteen minute cure at 160° C. was normally utilized. The exact sample configuration of the test specimens for the ozone testing varies by the description of the ASTM method utilized. Reference is made to the ASTM test methods and such methods are incorporated herein by reference to abbreviate the required descriptive information regarding specimen preparation, test methods and test results.

Rubber articles must be protected against ozone when they are subjected to exposure on outdoor weathering. One of the most difficult applications is on a tire where the vehicle remains out of doors and in ozone bearing atmosphere for an indefinite period of time. The true service conditions under which tires operate are not well duplicated by either static ozone tests such as those described in Table I and II nor are they well duplicated using dynamic test procedures such as DeMattia Flex Testing. In an effort to simulate a typical tire surface condition the following test method is utilized. In the testing scheme, samples are mounted in southern facing test fixtures outdoors, exposed to the full outdoor environmental conditions as are present in Naugatuck, Conn. The samples are continuously flexed for over approximately a 78° angle day after day until the deterioration as evidenced by the appearance and growth of cracks on the sample surface is observed and recorded. The test results are expressed in kilocycles. The samples are flexed through a 78° angle at about 8.5 kilocycles per hour.

This dynamic flexing test uses rectangular specimens 12 mm by 76 mm with a 3 mm radius circular groove across the center of the specimen.

It is apparent from the results, that Example 10 which contained no antiozonant survived less than 4400 kilocycles under this test. Examples 11, 12 and 13, which are protected by the pyrimidines of this invention, respectively, exhibited very significant improvements in the ability to withstand the outdoor aging.

FATIGUE FLEXING - EXAMPLES 15-19

This test method covers the determination of fatigue life of rubber compounds undergoing a tensile-strain cycle. During part of the cycle, the strain is relaxed to a zero value. The specimens are tested without intentionally initiated flaws, cuts, or cracks. Failure is indicated by a complete rupture of the test specimen.

The Fatigue Flexing Results are very critical results which have good correlation to tire carcass life properties. The Fatigue Flexing test results appear in Table II below. Examples 16, 17, 18 and 19 show flex fatigue values of 49.1, 37.5, 59.9 and 43.2, respectively, versus the much lower value of Example 15 which is missing the key component of the invention.

TABLE II

| | FATIGUE FLEXING (Results in Kilocycles) | | | | |
|---|---|---|---|---|---|
| EXAMPLE NO. | 15 | 16 | 17 | 18 | 19 |
| ANTIOZONANT | blank | Ex. 1 | Ex. 2 | Ex. 3 | Ex. 4 |
| Unaged ASTM-D-4482-85 Cam 14 Cured 18 min. at 302 F. | | | | | |
| Kilocycles | 29.9 | 49.1 | 37.5 | 59.9 | 43.2 |

NON-STAINING CHARACTERISTICS - EXAMPLES 20-24

Samples specimens were prepared using the test formulation set forth previously but without wax. The test formulation was compounded, mixed and cured into flat test sheets for subsequent analysis of discoloration and staining characteristics. The specific testing was conducted in accordance ASTM-D925-83 Method C. The Method C judges the degree of staining tendency of material by determining the amount of discoloration that occurs from the substrate material through a white lacquer coating which has been placed on the test sample. The test formulation previously set forth for all test samples of the invention was utilized. Once the test specimen was mixed and cured, it was coated with a veneer of white lacquer in accordance with the ASTM-D925 procedure. It was then exposed to a sun lamp light source in a suitable test chamber for a specified period of time. The Hunter Lab TM Colorimeter test apparatus was utilized to objectively determine the change in the color of the white lacquer during the four hour exposure to the sun lamp. ASTM D2244-79 titled "Color Differences of Opaque Materials", reports a number of characteristics by the standard difference letters a, b, and L. Since the staining characteristics of normal antiozonants are very extreme, the L color scale is reported below. The L color scale is a scale from 0 to 100 with a 0 value being totally black and a 100 value being pure white. Therefore the higher the L value, the whiter the sample. The Test formulation of Example 20 was prepared as a blank which contain no antiozonant Examples 21-24 contain the antiozonant of the invention described in Example 1,2, 3 and 4.

The test results of the five samples are presented below in Table III showing the Hunter "L" value after four hours of exposure.

TABLE III

| HUNTER "L" COLOR RESULTS | | | | | |
|---|---|---|---|---|---|
| EXAMPLE NO. | 20 | 21 | 22 | 23 | 24 |
| ANTIOZONANT | blank | Ex. 1 | Ex. 2 | Ex. 3 | Ex. 4 |
| | 87.50 | 87.08 | 86.88 | 86.58 | 84.86 |

The results shown above clearly show that the compounds of the invention of Example 1, 2, 3 and 4 had color values of 87.50, 87.08, 86.88 and 84.86, respectively, which is very close to 87.50 value reported for the blank of Example 20. Thus, the compounds of the invention are shown to have minimal diffusion staining which is an extremely unusual result for stabilizer of the amine class. Thus, the compounds of the invention can be advantageously utilized as antiozonants without the normal accompanying problems of diffusion staining and severe discoloration. This class of materials could be described as non-staining antiozonants.

The compounds of the invention may be used to good advantage with antioxidants and antiozonants of the prior art in blends to enhance particular properties. While the substituted pyrimidine compounds of the invention have been described herein only as antiozonants, it is clear that the materials may also function as antioxidants for rubber, thus providing protection against oxidative degradation as well as ozone protection. It is noted that when used as an antioxidant, the levels are typically much lower per hundred parts of rubber hydrocarbon than when antiozonant protection is required.

The 2,4,6-tris(N-substituted-p-phenylenediamino)-substituted pyrimidines can be most advantageously used in a tire as a component of any or all of the thermosetting rubber-containing portions of the tire. These include the tread, sidewall and carcass portions of a truck, passenger or off-road vehicle tire which also contain many different reinforcing layers therein. These components typically contain more than one thermosetting rubber polymer in a blend which must be protected from ozone degration, as well as oxidative attack.

Methods of incorporating these compounds into the tire are conventional and well known. These compounds also activate the cure of the rubber stock in which they are incorporated compared to conventional paraphenylenediamines.

Unsaturated polymers may be optionally protected against both oxidative and ozone degradation by blending the pyrimidine compounds of the invention with conventional antioxidants. Many classes of phenolics, amines, etc. function as antioxidants. The Index of Commercial Antioxidants and Antiozonants, 3rd Edition published by The Goodyear Tire and Rubber Company lists materials commonly viewed as materials having antioxidant properties, and is incorporated herein by reference. Representative classes of such antioxidant materials are sterically hindered phenols, alkyl-substituted diphenylamines, aryl-substituted diphenylamines, aralkyl-substituted diphenylamines, naphthylamines, reaction products of a diarylamine and a ketone, mono-phenols, bisphenols, polyphenols, hydroquinone derivatives, and polymerized quinolines. The antioxidant system may contain one or more of these materials. Optimal levels of addition (PHR) for the antioxidants can be easily determined through routine experimentation and may vary widely depending upon the end use application.

In view of the many changes and modifications that may be made without departing from principles underlying the invention, reference should be made to the appended claims for an understanding of the scope of the protection afforded the invention.

We claim:

1. A compound of the formula (I):

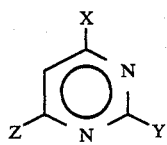 (I)

in which

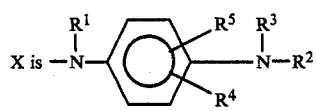

R¹ is hydrogen, $C_1$–$C_{11}$ alkyl, $C_3$–$C_6$ cycloalkyl, phenyl or phenyl substituted with $C_1$–$C_4$ alkyl or phenyl;

R² is $C_1$–$C_{11}$ alkyl, $C_3$–$C_6$ cycloalkyl or

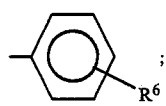

R³ is hydrogen, phenyl or $C_1$–$C_{11}$ alkyl when R¹ is hydrogen;

R⁴ is hydrogen or $C_1$–$C_8$ alkyl;

R⁵ is hydrogen or $C_1$–$C_8$ alkyl;

R⁶ is hydrogen, $C_1$–$C_{11}$ alkyl or $C_1$–$C_4$ alkoxy

Y is X, hydrogen, $C_1$–$C_4$ alkyl, —SH, SR⁷, —OH, OR⁷,

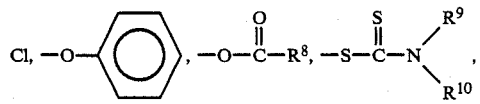

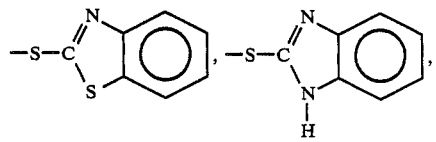

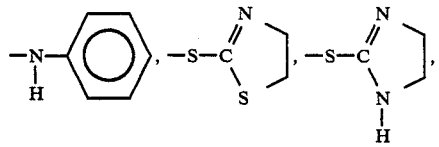

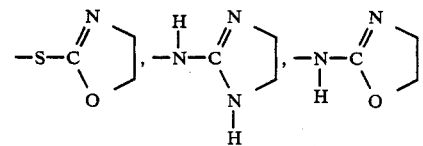

R⁷ is $C_1$–$C_{12}$;
R⁸ is $C_1$–$C_{11}$;
R⁹ and R¹⁰ are $C_1$–$C_4$ alkyl

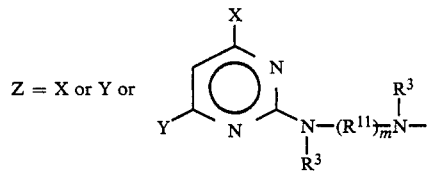

R¹¹ is $C_2$–$C_{10}$ linear alkyl; $C_5$–$C_{10}$ cycloalkyl or $C_7$–$C_9$ phenylaklyl;

m is 2–6

If Y≠X then R₆ can be hydrogen.

2. A 2,4,6-tris (N-alkyl para-phenylene diamino)-pyrimidine.

* * * * *